United States Patent [19]

Albery et al.

[11] Patent Number: 5,462,645
[45] Date of Patent: Oct. 31, 1995

[54] DIALYSIS ELECTRODE DEVICE

[75] Inventors: John W. Albery, Oxford; Peter T. Galley, Crowthorne, both of England

[73] Assignee: Imperial College of Science, Technology & Medicine, London, United Kingdom

[21] Appl. No.: 211,080

[22] PCT Filed: Sep. 21, 1992

[86] PCT No.: PCT/GB92/01736

§ 371 Date: May 18, 1994

§ 102(e) Date: May 18, 1994

[87] PCT Pub. No.: WO93/05701

PCT Pub. Date: Apr. 1, 1993

[30] Foreign Application Priority Data

Sep. 20, 1991 [GB] United Kingdom ............... 9120144

[51] Int. Cl.$^6$ ..................................... G01N 27/26
[52] U.S. Cl. .................. 204/153.12; 204/153.1; 204/415; 204/403; 204/409; 204/412; 128/642
[58] Field of Search ................... 204/415, 403, 204/412, 409, 231, 263, 153.1, 153.12; 128/642; 435/817, 291, 288

[56] References Cited

U.S. PATENT DOCUMENTS

| | | | |
|---|---|---|---|
| 4,490,234 | 12/1984 | Buzza | 204/415 |
| 4,797,180 | 10/1989 | Schneider et al. | 204/412 |
| 5,106,365 | 4/1992 | Hernandez | 604/27 |
| 5,191,900 | 3/1993 | Mishra | 128/769 |
| 5,217,112 | 6/1993 | Almon | 204/412 |
| 5,332,479 | 7/1994 | Venoyama et al. | 204/403 |

FOREIGN PATENT DOCUMENTS

| | | |
|---|---|---|
| 2013895 | 8/1979 | United Kingdom . |
| 2130916 | 6/1984 | United Kingdom . |

Primary Examiner—John Niebling
Assistant Examiner—Bruce F. Bell
Attorney, Agent, or Firm—Bell, Seltzer, Park & Gibson

[57] ABSTRACT

A dialysis electrode device comprises a shank of needle-like proportions and formed from a hollow dialysis fiber membrane. The shank is closed at its distal end by a sealing plug and, at its proximal end, it is sealed to and in communication with an auxiliary chamber defined by a tubular body part. Electrolyte is supplied to the chamber in the shank through an inlet conduit and is removed via an outlet conduit connected to the auxiliary chamber. The device also includes a dialysis or first working electrode, which is insulated save for a length thereof disposed within the hollow shank, a counter electrode and a reference electrode mounted within the auxiliary chamber. It may be used in clinical medicine and the food, pharmaceutical and other industries where it is desirable to analyze or monitor the presence of chemical substances. In carrying out a microdialysis procedure in human tissue, for example, the device is primed with an enzyme electrolyte solution and electrical measurements are taken, in situ, of the concentration of a chemical substance diffusing into the shank chamber through the dialysis fiber shank.

11 Claims, 2 Drawing Sheets

DIALYSIS ELECTRODE DEVICE

FIELD OF THE INVENTION

The present invention relates to a dialysis electrode or biosensor device suitable for use in medicine and the food, drink, pharmaceutical and environmental monitoring industries and other industries where it is desirable to analyse or monitor the presence of chemical substances.

Dialysis is a general sampling technique which can be used in conjunction with an appropriate analytical technique, such as electrochemical analysis, to analyse chemical substances recovered by the dialysis. Microdialysis is a technique for sampling in vivo body fluids, for example, as described in an article by Urban Ungerstedt entitled "Microdialysis—A New Bioanalytical Sampling Technique" published in Current Separations, Volume 7, No. 2 (1986) by Bioanalytical Systems, Inc. It may be used in the electrochemical analysis of chemical substances extracted from the brain and various other organs of the human or animal body. With this technique, a chemical substance diffuses into a microdialysis probe, which may be the size of a syringe needle, implanted in tissue and the concentration of the substance is determined outside the body. Particularly, the introduction of a microdialysis probe into the brain makes it possible closely to monitor the chemical events of the extracellular space, wherein chemical transmission involved in neurotransmission of information takes place.

BACKGROUND OF THE INVENTION

The problems with the dialysis technique are threefold. Firstly, the dialysate is diluted into a flowing stream. Therefore, in order to have a sufficient quantity to measure, typically, a sample must be collected over ten to twenty minutes. This leads to the second problem that the technique has poor time resolution. Thirdly, the continuous removal by dialysis disturbs the concentration of the perfusing species in the region of the probe. With a view to resolving the problem of slow response time, it has been proposed to use an on-line electrode for the analysis but even so there is a delay whilst the solution flows slowly from the probe to the electrode in the electrochemical analysing equipment.

Fast response times of less than half a second may be obtained from implanted enzyme electrodes. However, the general problem with such implanted electrodes, in which an enzymic reaction is monitored by sensing changes in electrical parameters, is that the enzyme becomes inactive. It is also not easy to supply a cofactor, such as, NADH (reduced form of nicotinamide adenine dinucleotide). Furthermore, toxicity may be a barrier to use in clinical practice.

SUMMARY OF THE INVENTION

It is an object of the present invention to alleviate the problems experienced with hitherto known dialysis and electrode techniques of sampling and to provide a analysis electrode device which produces rapid measurements of variations in the concentrations of chemical substances and, more particularly, the in vivo concentrations of chemical substances, such as, the important neurotransmitter, glutamate, occurring in the extracellular space in a human or animal brain.

The present invention consists in a dialysis electrode device comprising a hollow probe having an internal chamber and a dialysis membrane forming a wall of the chamber, a working electrode mounted in the chamber, conduit means for supplying electrolyte to the chamber and removing electrolyte therefrom, and a reference electrode arranged to be electrically coupled to the working electrode by the electrolyte.

Conventional dialysis requires the continuous flow of perfusing solution as, for example, in the case of carrying out dialysis with a probe implanted in the brain or any other organ of a human or animal body, and relatively large amounts of chemical substances may be removed. With the present invention, the dialysis electrode device may simply be primed intermittently with a flow of electrolyte solution and electrical measurements of a particular dialysate are made with the probe remaining in situ in the organ. Because measurements are made when there is no flow through the device, disturbance of the organ tissue is minimised. Also, when the device is not in use all enzyme may be removed to prevent any depletion.

Conventional platinum electrodes may be used or conducting organic salts or other mediators, such as, TTFTCNQ (tetrathiofulvalene-tetracyano-p-quinodimethane) or NMPTCNQ (is N-methylphenazinium-tetracyano-p-quinodimethane), can be electrochemically plated onto the working electrode. A target molecule, such as, glutamate diffuses through the dialysis membrane. Instead of being carried away by the flowing solution, it is immediately consumed by the in situ enzyme electrode. Using a dialysis pump connected to the conduit means, the solution around the electrode can readily be changed. This means that the electrode can be supplied with fresh enzyme and cofactor, as well as different enzyme solutions, thereby enabling the performance of control and test measurements. It can also be replated with the same or a different mediator.

Accordingly, the present invention alleviates the problem of short lifetime hitherto experienced with the enzyme electrodes of known electrochemical biosensors. Furthermore, it enables good time resolution and sensitivity to be achieved and the control of the in vivo environment of the working electrode. The device may also be made biocompatible.

Electrochemical enzyme electrodes of prior electrochemical biosensors can only measure one chemical substance because a preselected enzyme is immobilised on the electrode. The present invention enables different enzyme loaded liquids to be used as electrolyte solutions to detect different chemical substances. For example, the invention can be used to detect glutamate or acetylcholine in neurology applications, glutamate or ascorbate in the food industry and glucose in clinical diagnoses in vitro. In a modification of the invention, the device may be filled with dry powder enzyme as an electrolyte for emergency purposes.

The invention has two further advantages. Firstly, by flowing a known concentration of target analyte over the working electrode and making test measurements, the device can be calibrated so that it measures absolute, as opposed to relative, concentrations of analyte. This is impossible with conventional implanted enzyme electrodes or with conventional dialysis. Secondly, electrical current transmitted by interfering substances, such as, ascorbate in the case of brain microdialysis, can be mitigated or blocked by surrounding the working electrode with a suitable second enzyme. For example, in the case of microdialysis of the brain, interference from ascorbate may be blocked by using ascorbate oxidase.

Measurements of the analyte concentration may be produced by means of a potentiostat connected to the working and reference electrodes of the dialysis electrode device.

With this potentiometric method of measurement, the potential difference between the two electrodes is measured, when no current flows. As an alternative to the potentiometric method, current flow measurement is preferred as this results in reduced errors. In this regard, the dialysis electrode device, preferably, includes an auxiliary or counter electrode arranged to be electrically coupled to the working electrode by the electrolyte with this preferred method of measurement, the electrical current, caused by oxidation of the enzyme, is measured as it flows between the working and counter electrodes, the reference electrode being used to retain the working electrode at a predetermined potential.

The dialysis electrode device may include a second working electrode which may be useful for compensating for spurious electrical signals, as well as measuring interference from electroactive molecules.

Conveniently, the probe comprises a semi-permeable dialysis membrane formed as a needle-like hollow shank, closed at its distal end. Such a configuration facilitates introduction of the probe into the matter to be tested. The shank may be made of suitable size for microdialysis procedures, for example, not greater than 250 µm for neurophysiclogical work. The length of the shank can be selected so that the probe alone, and no other parts of the device, is implanted in the test matter, thereby minimising any damage caused by introduction of the probe. The passage in the hollow shank constitutes the internal chamber and the conduit means may comprise an inlet conduit projecting into the passage to a position adjacent the distal end of the shank and an outlet conduit connected to the proximal end of the shank. At its proximal end, the hollow shank may be connected to an auxiliary chamber to which the outlet conduit is connected. The auxiliary chamber may also house the reference electrode and/or counter electrode. The second working electrode, if provided, may be spirally wound about the outside of the shank.

BRIEF DESCRIPTION OF THE DRAWINGS

In order that the present invention may be more readily understood, reference will now be made to the accompanying drawings, in which.

DESCRIPTION OF THE PREFERRED EMBODIMENTS

Figure 1:
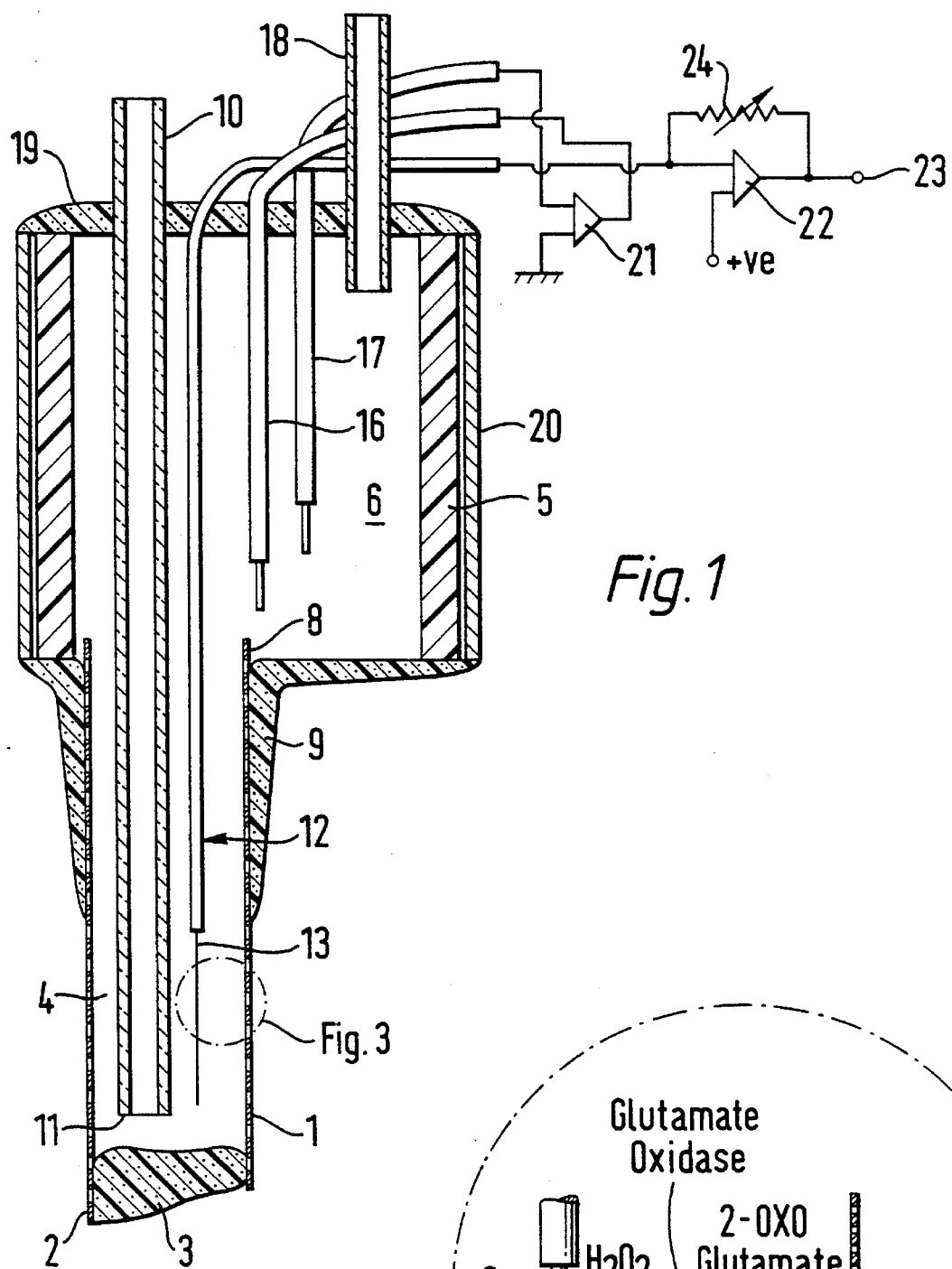
FIG. 1 schematically illustrates an axial section through a microdialysis electrode device constructed in accordance with the invention.

Referring to FIG. 1 of the drawings, the device comprises a shank 1 of needle-like configuration and formed from a hollow, semi-permeable, dialysis, fiber membrane. The shank 1 is closed at its distal end 2, which may be pointed, by an epoxy resin plug 3. The passage within the hollow dialysis fiber shank 1 constitutes an internal chamber 4 and, at its proximal end, the shank is connected to a tubular plastics body part 5, for example, made from polyethylene tubing, which defines an auxiliary chamber 6 communicating with the internal chamber 4 of the hollow shank. The shank and body 1,5 are arranged with their axes mutually parallel and with the shank disposed eccentrically with respect to the body. The body is sealed to the proximal end 8 of the shank by means of a suitable sealing material 9, such as an epoxy sealing material, and is encased in a tubular housing 20 made from a stiffening material, such as stainless steel or glass tubing.

Projecting axially through the tubular body 5 and into the chamber 4 of the hollow shank is an inlet conduit or cannula 10 for supplying electrolyte solution to the chamber. The outlet end 11 of the inlet conduit 10 terminates at a position adjacent the distal end 2 of the shank, and spaced a small distance from the plug 3. Juxtaposed the inlet conduit 10 is a dialysis or first working electrode 12 which is insulated save for a length 13 thereof disposed within the dialysis fiber shank 1. A counter electrode 16 and a reference electrode 17 are also mounted in the auxiliary chamber 6.

Electrolyte solution supplied to the chamber 4 in the dialysis fiber shank 1, via the inlet conduit 10, flows from the outlet end 11 thereof, through the chamber 4 and about the working electrode 12, and is removed from the device via the proximal end 8 of the shank, the auxiliary chamber 6 and an outlet conduit or cannula 18 projecting from the opposite end of the tubular body 5 to the shank. The electrodes 12, 16, 17 and conduits 10,18 are secured in position at this opposite end of the tubular body 5 by a suitable epoxy sealing material 19, such as cyano acrylate sealing material.

Figure 2:
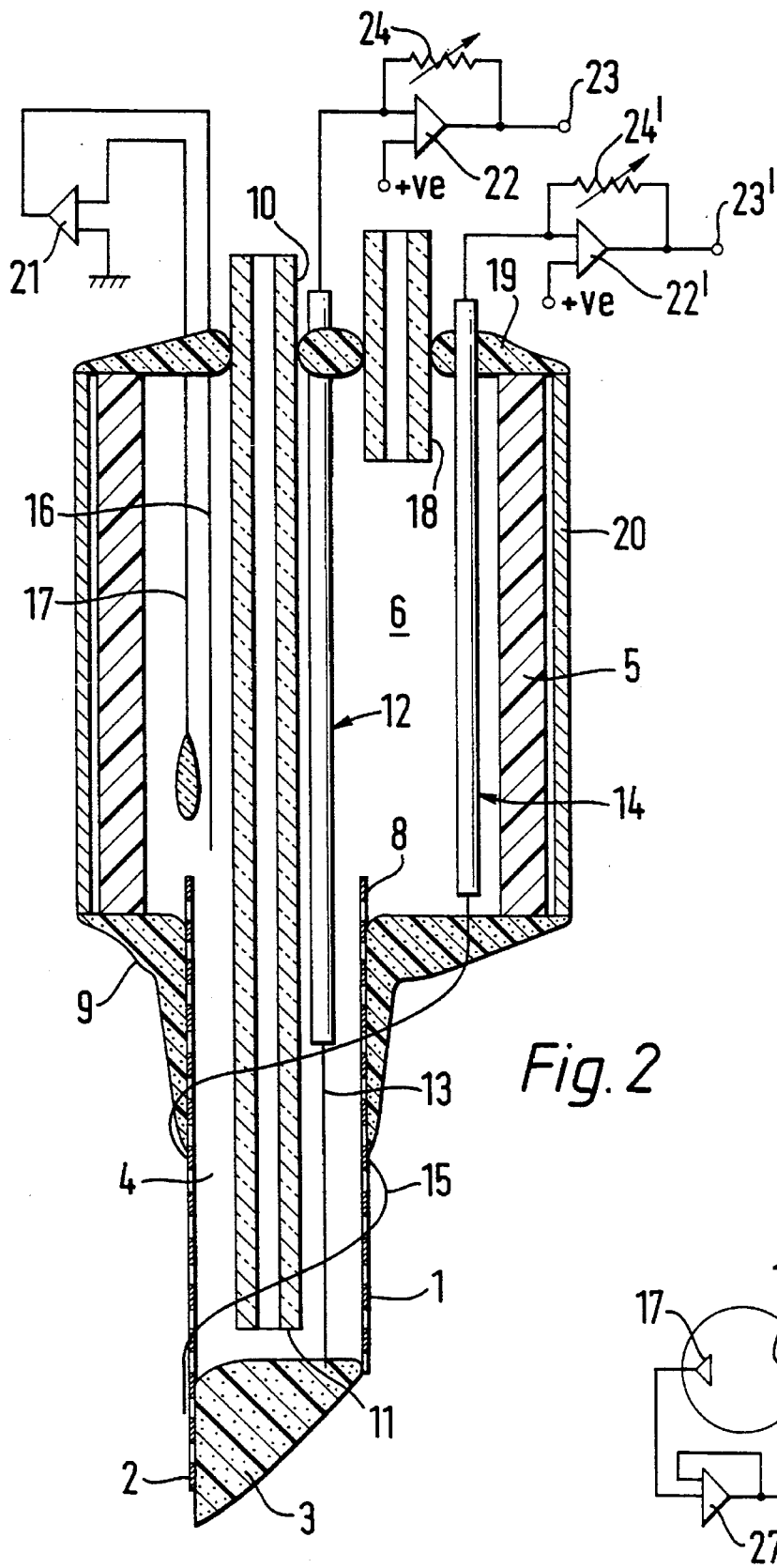
FIG. 2 is an axial section similar to FIG. 1 and illustrating modifications.

In a modified embodiment illustrated in FIG. 2, like reference numerals indicate similar parts to those of FIG. 1. In this modified embodiment, the distal end of the uninsulated length 13 of the working electrode 12 is embedded in the epoxy plug 3 and the electrode serves as an internal reinforcing strut for the shank 1. Furthermore, a second working electrode 14 extends through the tubular body 5 and the sealing material 9 and is spirally wound about the exterior of the shank 1. The insulation of the electrode 14 is removed from the length 15 of the electrode wound about the shank.

in a typical dialysis electrode device as illustrated in FIGS. 1 or 2, the dialysis membrane is made of cellulose. An upper length of the membrane of approximately 5 mm is coated with the epoxy resin sealing material 9 leaving a probe length of approximately 4 mm. The working electrode 12 may, for example, be Teflon coated platinum wire, with approximately 4 mm of Teflon being removed from the distal end of the electrode to expose the length 13 of platinum wire. The reference electrode may be an Ag/AgCl electrode made from 75 µm Teflon coated silver wire, whilst the counter electrode 16 may be a silver electrode. The conduits 10,18 may be vitreous silica conduits. In one embodiment suitable for microdialysis procedures, the tubular body 5 has an external diameter of approximately 1 mm, the tubular casing 20 has an external diameter of 1.5 mm, the hollow dialysis fiber shank 1 has an external diameter of 220 µm, the inlet conduit 10 has an external diameter of 140 µm, the first working electrode 12 is insulated 50 µm platinum wire and the second working electrode 14 is insulated 25 µm platinum wire.

Schematically illustrated in FIG. 1 is the electrical circuitry via which electrical energy is supplied to the electrodes 12,16,17 and the electrical current in the working electrode 12 is detected in order to provide a measurement of the quantity of analyte diffused through the dialysis fiber shank 1 into the electrolyte contained in the chamber 4. The reference and counter electrodes 17,16 are interconnected via an amplifier 21 having its inputs connected to the reference electrode and ground and its output connected to the counter electrode. This arrangement maintains the counter electrode 16 at a fixed potential with respect to the reference electrode 17 and ground. The working electrode 12 is connected to one input of an amplifier 22 having its other input connected to a suitable electrical source for applying a potential difference between the input and ground and, hence, across the electrodes. The output terminal 23 of the amplifier 22 is connected to a suitable device (not shown) for detecting the current flow through the working electrode and providing a measurement of the quantity of analyte diffused into the chamber 4. The variable resistor 24 connected across the amplifier provides for gain control.

In the embodiment of FIG. 2, the electrical potential is applied to the second working electrode 14 and the current flow in this electrode is measured by circuitry 22',23',24' similar to the circuitry 22,23,24 connected to the first working electrode 12.

Figure 4:
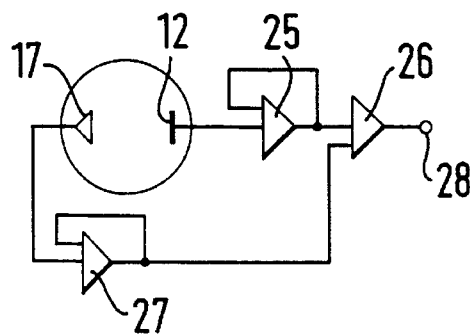
FIG. 4 is a schematic illustration of a potentiometric measuring circuit which may be used with the invention.

Alternatively to the current measuring systems shown in FIGS. 1 and 2, analyte may be measured by a potentiometric system as schematically illustrated in FIG. 4. In this event, the counter electrode 16 is not required and the reference electrode 17 is interconnected with the working electrode by the electrical circuitry. Hence, the working electrode 12 is connected to the positive input of a first amplifier 25 having its negative input connected to the output of this first amplifier. The output of the first amplifier 25 is also connected to the negative input of a second amplifier 26, the positive input of which is connected to the output of a third amplifier 27 having its positive input connected to the reference electrode 17. The negative input of the third amplifier 27 is connected to its output. Changes in potential are detected at the output terminal 28 of the second amplifier 26 in order to produce an electrical signal representative of the quantity of analyte diffused through the dialysis fiber shank 1.

In carrying out a microdialysis procedure in the brain, for example, the shank 1 is introduced into the required position in the brain and its length can be predetermined so that the shank, alone, and not the wider tubular body part 5, is implanted thereby minimising any damage caused. The electrodes 12,14,16,17 are connected to electrical measuring circuitry, as described above, all potentials being reported with respect to the reference electrode 17. The inlet and outlet conduits 10,18 are connected to a suitable microdialysis pump capable of pumping electrolyte solution into the probe at a flow rate of, for example, 0.5 mm$^3$ per min. The device is intermittently primed with an enzyme electrolyte solution, with the added advantage that fresh enzyme can be introduced when required or, as described below, mixtures of enzymes can be used, and electrical measurements are taken in situ of the concentration of a chemical substance diffusing into the shank chamber 4 through the dialysis fiber membrane 1. The latter may be designed to allow or prevent flow of predetermined chemical substances.

In carrying out a microdialysis procedure in the brain, two different techniques for measuring glutamate may be utilised. Firstly, a TTFTCNQ modified working electrode 12 may be used or, secondly, a platinum electrode. Utilising the TTFTCNQ electrode as a mediator has the advantage of working at a low potential, reducing interference from some electroactive species, although ascorbate, the main interferent, is oxidized very effectively. With the second technique, oxidation of hydrogen peroxide has proved to be more reliable for measuring glutamate, resulting in a glutamate sensor with a 100% activity over a three day period. With a TTFTCNQ electrode 12, the device is fully active for only one day.

Figure 3:
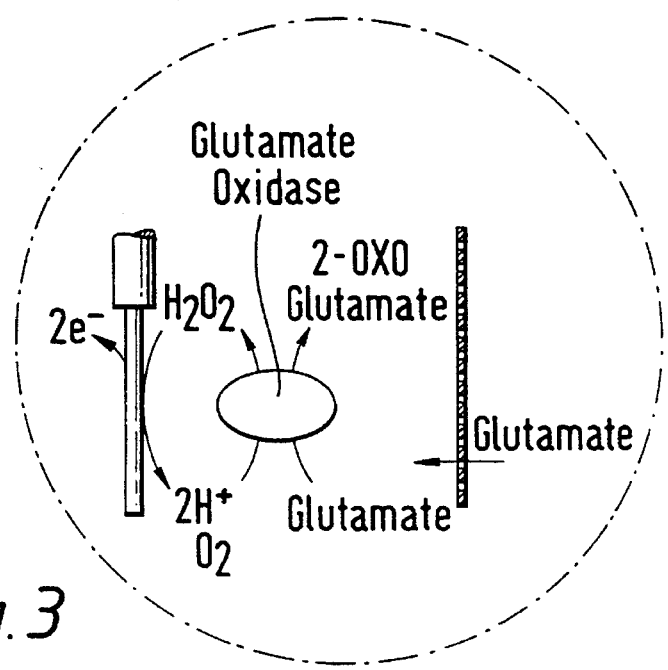
FIG. 3 is a diagram illustrating the reaction scheme when the electrode device of FIG. 1 is used to measure glutamate.

With the peroxide system (see FIG. 3), the background electrolyte may be Krebs Ringer buffer which consists of the following mmol dm$^{-3}$ concentrations, that is, Na Cl 136, KCl 2.54, KH$_2$PO$_4$ 1.18, NaHCO$_3$ 16, CaCl$_2$ 1.18, MgSO$_4$ 1.18 and glucose 10. The pH was adjusted to 7.4. All chemicals were of AnalaR quality (AnalaR is the trade name of British Drug Houses for its purest reagents). To measure glutamate, the enzyme glutamate oxidase is added to the buffer solution. A typical activity is 0.4 U mm$^{-3}$. The electrical current from oxidising the product of the enzyme reaction, hydrogen peroxide, is measured at a potential of 650 mV. Current voltage curves show that this potential gives a limiting current.

The disadvantage of the peroxide system is the high potential used for oxidation of the hydrogen peroxide. At this potential, there is considerable oxidation of electroactive interferents, such as, ascorbate, uric acid and HVA (homovanillic acid). In order to reduce interference from ascorbate, the working electrode 13 may be coated with Nafion or other suitable polymers. Tests also show that ascorbate can be removed with ascorbate oxidase and that the other interferents are either at a very low concentration or that their levels are stable enough so as not to interfere with the measurement of glutamate.

With the dialysis electrode device of FIG. 2 having the second working electrode 14 and the probe chambers 4,6 containing both glutamate and ascorbate oxidases, the first working electrode 12, an internal platinum electrode, measures enzymatically generated peroxide and, hence, measures glutamate, and the second working electrode 14, an external platinum electrode, measures ascorbate but not glutamate. The device can be calibrated beforehand in vitro in the concentration range of interest for the in vivo measurements so that it can then be used to produce measurements which indicate to a neurophysiologist how either or both glutamate and ascorbate vary with time.

The peroxide system, is about 100 to 1000 times more sensitive that the TTFTCNQ technique. Tests in which the device is utilised as a glutamate sensor have shown real time measurement of glutamate changes during a response to a behavioural stimulus. This type of work has hitherto been impossible because there was no suitable method for measuring glutamate changes over short periods. Previously, glutamate had to be measured by one of three techniques:

(1) derivatization with an absorbing marker followed by HPLC (high pressure liquid chromatography) separation.

(2) Amino acid analysis or (3) Enzymatic assay using glutamate dehydrogenase, measuring the NADH produced.

These prior methods rely on removal of samples from the biological tissue, which not only dilutes the glutamate but also requires long sampling intervals in order for sufficient glutamate to be collected.

The sensitivity of the three prior techniques (about nM) is lower than that produced by the device according to the present invention (about 100 nM), but this is unlikely to be a significant problem as physiological changes in glutamate are of the order of 1–2 µM. In any case, the temporal resolution of the present device, that is 1 sec. compared to 20 min., outweighs any sensitivity advantage.

The main advantage of a dialysis electrode device as described above is the ability to control the local environment of the implanted electrode. Firstly, by using different enzymes one can select the analyte of choice in the same animal for the same probe. Secondly, ascorbate interference is removable so that, for the first time, sufficient sensitivity and time resolution is achieved and real time variations in glutamate levels can be measured. Thirdly, change in glutamate levels in response to a mild behavioural stimulus can be measured. As a result, neurochemical changes may be linked with behavioural studies.

By suitable choices of enzymes, the electrode device may be used to measure real time changes in concentration of a wide variety of metabolites. For instance, good in vitro calibration plots have been obtained for glucose using glucose oxidase and for acetylcholine using acetyl choline esterase followed by choline oxidase. This provides the prospects of measuring metabolites such as these in vivo in the practice of clinical medicine.

Whilst particular embodiments have been described, it will be understood that modifications may be made without departing from the scope of the invention as defined by the appended claims.

We claim:

1. A dialysis electrode device for monitoring the presence of an analyte in test matter comprising:
   (a) probe means for implanting in said test matter, said probe means including a hollow shank formed from a hollow fiber of dialysis membrane material, said hollow shank having an internal chamber delimited by said dialysis fiber membrane, a proximal end and a closed distal end,
   (b) conduit means for supplying electrolyte to said probe means and removing electrolyte therefrom, said conduit means including an inlet conduit for said electrolyte extending into said chamber in said hollow shank to a location adjacent said distal end of said hollow shank, and an outlet conduit in communication with said proximal end of said hollow shank,
   (c) a working electrode mounted in said probe means and extending into said chamber in said hollow shank to a location adjacent said distal end of said hollow shank, and
   (d) a reference electrode mounted in said probe means and electrically coupled to said working electrode by said electrolyte supplied to said chamber via said conduit means.

2. A device as claimed in claim 1, including a counter-electrode which is electrically coupled to said working electrode by said electrolyte.

3. A device as claimed in claim 1, including a second working electrode which can compensate for spurious electrical signals and measure interference from electroactive molecules.

4. A device as claimed in claim 3, wherein said second working electrode is disposed on an external surface of said hollow fiber.

5. A device as claimed in claim 1, including a hollow body part integrally joined to said proximal end of said hollow shank and having an auxiliary chamber communicating with said chamber in said hollow shank, and wherein said reference electrode is disposed in said auxiliary chamber and said outlet conduit has an inlet end disposed in said auxiliary chamber.

6. A device as claimed in claim 5, including a counter-electrode disposed in said auxiliary chamber, said counter-electrode being electrically coupled to said working electrode by said electrolyte.

7. A device as claimed in claim 5, including a second working electrode spirally wound about said hollow fiber.

8. A method of monitoring the presence of an analyte in test matter, in which said analyte is separated from the test matter by diffusion through a dialysis membrane comprising the steps of:
   (a) providing a dialysis electrode device having probe means including a hollow shank formed from a hollow fiber of dialysis membrane material and having an internal chamber delimited by said hollow fiber and a closed distal end, said probe means including conduit means for supplying electrolyte to said chamber and removing electrolyte therefrom, a working electrode extending into said chamber and a reference electrode,
   (b) implanting said hollow shank in said test matter,
   (c) supplying electrolyte to said chamber via said conduit means,
   (d) separating said analyte from said test matter by diffusion through said dialysis fiber membrane and into said electrolyte,
   (e) applying a potential difference between said electrodes, and
   (f) detecting a resulting electrical signal in said working electrode to produce a signal representative of the concentration of said analyte diffused through said dialysis fiber membrane.

9. A method as claimed in claim 8, wherein said electrolyte includes a chemical substance for alleviating the effect, on the detection of said analyte, of an interferant, and wherein a potential difference is applied between said electrodes and a second working electrode disposed externally of said dialysis fiber membrane, and a resulting electrical signal in said second working electrode is detected to produce a signal representative of said concentration of said interferant.

10. A method as claimed in claim 8, wherein the supply of said electrolyte to said chamber is stopped at least during said detecting step.

11. A method as claimed in claim 8, wherein at least one enzyme is supplied to said chamber together with said electrolyte.

* * * * *